Figure 1:
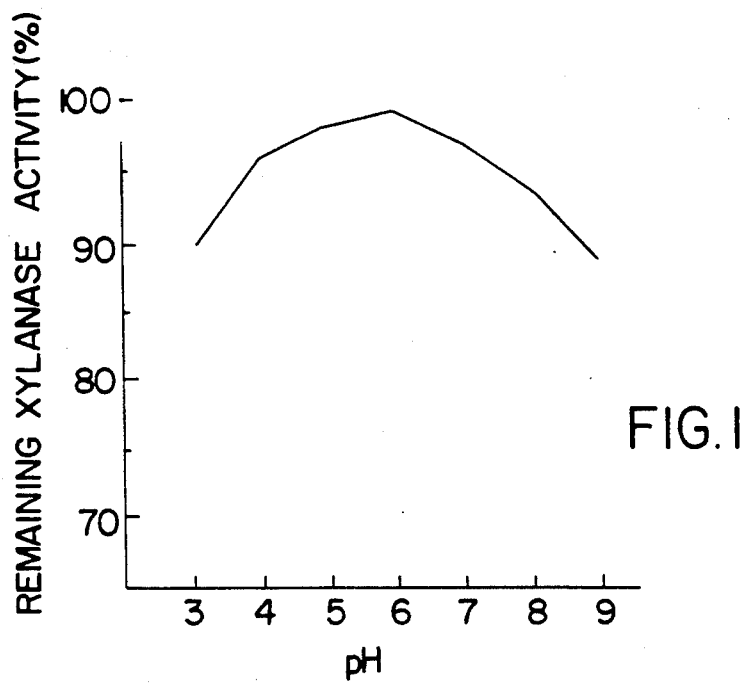

United States Patent [19]

Wizani et al.

[11] Patent Number: 5,183,753
[45] Date of Patent: Feb. 2, 1993

[54] **PREPARATION OF XYLANASE BY CULTIVATING *THERMOMYCES LANUGINOSUS* DSM 5826 IN A MEDIUM CONTAINING CORN COBS**

[75] Inventors: Wolfgang Wizani, Steyr; Hermann Esterbauer; Walter Steiner, both of Graz, all of Austria; Joseph Gomes, Dhaka, Bangladesh

[73] Assignee: Voest-Alpine Industrienlagenbau Gesellschaft m.b.H., Linz, Austria

[21] Appl. No.: 696,943

[22] Filed: May 8, 1991

[30] Foreign Application Priority Data

May 8, 1990 [AT] Austria .................. 1030/90

[51] Int. Cl.$^5$ .................. C12N 9/00; C12N 9/24; C12N 9/26; C12N 1/14
[52] U.S. Cl. .................. 435/201; 435/183; 435/200; 435/911; 435/254
[58] Field of Search .................. 435/200, 201, 911, 183, 435/254

[56] References Cited

U.S. PATENT DOCUMENTS

| | | | |
|---|---|---|---|
| 4,568,644 | 2/1986 | Wang et al. | 435/161 |
| 4,725,544 | 2/1988 | Tan et al. | 435/200 |
| 4,746,517 | 5/1988 | Ducroo | 426/12 |
| 5,023,176 | 6/1991 | Ducroo | 435/105 |

FOREIGN PATENT DOCUMENTS 1353342  2/1990  European Pat. Off.

OTHER PUBLICATIONS

Biotechnology Letters, vol. 10, No. 12, 907–912 (1988).
American Type Culture Collection Catalogue (Fungi/Yeast), 17th Edition (1987), p. 377.
Chemical Abstract, vol. 100, 155166r (1984) and therein cited Kitpreechavanich et al., J. Jerment Technol. vol. 62, No. 1, p. 63–69 (1984).
Chemical Abstracts, vol. 107, 38028f (1987) and therein cited W. Grajek, Biotechnol. Lett. vol. 9, No. 5, pp. 353–356 (1987).
Chemical Abstracts, vol. 113, 57395p (1990) and therein cited L. Anand et al., Indian Journal of Experimental Biology, vol. 28, May, 1990, pp. 434–437.
Purification and Properties of Xylanase from the Thermophilic Fungus, Humicola lanuginosa (Griffon and Maublanc) Bunce, vol. 276, No. 2, pp. 546–553.

*Primary Examiner*—David M. Naff
*Assistant Examiner*—Mike Meller
*Attorney, Agent, or Firm*—Wenderoth, Lind & Ponack

[57] ABSTRACT

Xylanase is prepared by cultivation of a fungus in a nutrient medium which contains corn cobs. The fungus is preferably *Thermomyces lanuginosus* DSM 5826 which produces an exo- and endo- cellulase-free xylanase.

5 Claims, 2 Drawing Sheets

PREPARATION OF XYLANASE BY CULTIVATING *THERMOMYCES LANUGINOSUS* DSM 5826 IN A MEDIUM CONTAINING CORN COBS

The invention relates to a process for the preparation of xylanase, to the use thereof, to the microorganism *Thermomyces lanuginosus* DSM 5826 and to exo- and endocellulase-free xylanase produced by the latter.

The breakdown, of hemicellulose, which is mainly composed of xylan in the case of annual plants or deciduous trees, is a step which is necessary in the production of cellulose. This breakdown can be carried out either by chemical means, for example by hot alkaline extraction, or by enzymatic means by treatment with substrate-specific enzymes, specifically with xylanases. Enzymatic treatment of unbleached or semibleached pulp with xylanases results in breakage of hemicellulose linkages and breakdown of xylan. However, it is possible to employ for this purpose only pure xylanases which contain no cellulase impurities because otherwise cellulose is also cleaved and broken down, which is extremely undesirable.

Xylanases which break down and utilize as C source the xylan-containing raw materials present in the nutrient medium are produced by, inter alia, a number of mesophilic and thermophilic microorganisms. However, depending on the other raw materials present in the nutrient medium, predominantly cellulose, the cellulases specific for this substrate are also produced. In order to obtain exo- and endocellulase-free xylanase it is necessary to separate and purify the xylanase from the produced cellulases in an elaborate process. In order to reduce the production of cellulases during fermentation, the microorganisms can also be cultivated on purified xylan. The use of xylanases which have been obtained from *Trichoderma harzianum* cultivated on purified xylan for the selective breakdown of xylan is described in D. J. Senior et al., Biotechnology Letters, Vol 10, No. 12, p. 907–912 (1988). However, cultivation on highly pure xylan is unsuitable because of the high costs of raw materials.

It has now been found, unexpectedly, that xylanase with surprisingly high activity is produced when a fungus is cultivated in a nutrient medium which contains corn cobs, with the resulting xylanase displaying only very low or no exo- and endocellulase activities.

The invention therefore relates to a process for the preparation of xylanase, which is characterized in that a fungus is cultivated in a nutrient medium which contains corn cobs.

Xylanase is produced according to the invention by cultivation of a fungus in a nutrient medium which contains corn cobs. By xylanase is meant in this context only those xylanases which display only very low or no exo- or endocellulase activities. The fungi which can be employed therein are those fungi which are able to produce high xylanase activities in the process according to the invention. One example of such fungi is *Thermomyces lanuginosus*. A strain of the order Moniliales was isolated from a pile of jute waste in a jute factory in Bangladesh in which jute fibers are treated with an oil emulsion. The temperature in the pile of jute waste was 65° to 70° C. This strain has been deposited at the Deutsche Sammlung von Mikroorganismen und Zellkulturen under DSM 5826. This strain is particularly suitable for producing xylanase with surprisingly high activity in a nutrient medium which contains corn cobs. *Thermomyces lanuginosus* DSM 5826 is new, and the invention likewise relates to it.

The nutrient medium in which the fungus is cultivated contains corn cobs besides the nutrients and trace elements necessary for growth. The corn cobs can be employed as such or ground and, where appropriate, sterilized by heating to 110° to 130° C. or by pretreatment with, for example, superheated steam. Particularly high xylanase activities are, surprisingly, achieved when the corn cobs are coarsely ground before they are used. Although the results are still surprisingly good if the corn cobs are shredded or finely ground, the use of coarsely ground corn cobs showed surprising results. Suitable nitrogen sources are, for example, meat peptone, fish peptone, urea, ammonium sulfate, malt extract, meat extract, soya bean meal, yeast extract and the like, inorganic salts, for example, potassium bisulfate, potassium dihydrogen phosphate, disodium hydrogen phosphate, iron sulfate, calcium chloride, magnesium sulfate and the like. In order to increase the rate of release of xylanase into the nutrient medium it may be advantageous to add surface-active substances. Normally, non-ionic surface-active substances, for example Tween 40, Tween 60 or Tween 80, are employed in an amount of 0.05 to 0.5% by weight based on the total amount of the medium. It is also possible, where appropriate, to add trace elements, for example uncommon metals such as $Mn^{2+}$, $Zn^{2+}$, $Fe^{2+}$ or vitamins, to the medium. The medium is, where appropriate, advantageously adjusted to a pH of 5.0 to 8.0, preferably to 6.0 to 7.0, with ammonia or phosphoric acid.

The fungus is cultivated in the nutrient medium at a temperature of about 30° to 70° C., preferably at 40° to 60° C., particularly preferably at 45° to 55° C. It is unnecessary to keep constant the pH set at the start of the fermentation. However, where appropriate, it can also be kept constant by metering in, for example, ammonia or phosphoric acid.

After completion of the fermentation, the xylanase can be isolated from the fermentation process in a conventional manner. For this, for example, fungal mycelium, spores and remaining undissolved substances are removed by centrifugation or filtration. The enzyme can be further purified in a conventional manner, for example by filtering out with ammonium sulfate or by solvent precipitation with acetone, alcohol or the like. The crude enzyme obtained in this way can, where appropriate, be further purified, for example by gel filtration, ion exchange chromatography, gel electrophoresis and the like.

The xylanase prepared according to the invention has a high xylanase activity. It has emerged that surprisingly high xylanase activities can be achieved on use of corn cobs by comparison with other untreated raw materials such as barley spelts, wheat straw, wheat bran, ground beech bark, alfalfa meal, red clover/grass meal, soya bean oil as C source. The activity of the produced xylanase is further increased by a multiple when coarsely ground corn cobs are employed.

The xylanase prepared according to the invention contains only low or no exo- and endocellulase activities. The xylanase produced by *Thermomyces lanuginosus* DSM 5826 has proved in several assays to be exo- and endocellulase-free. Such an exo- and endocellulase-free xylanase is new, and the invention likewise relates to it. Moreover, *Thermomyces lanuginosus* DSM 5826 is able to produce this xylanase not only in a nutrient medium which contains corn cobs but also in a nutrient medium which, in place of corn cobs, contains other solid or dissolved xylan-containing carbon sources such as, for example, barley- spelts, ground wheat straw, unbleached cellulose or xylan itself. However, surprisingly high xylanase activities are obtained with corn cobs in the nutrient medium.

The exo- and endocellulose-free xylanase according to the invention had the following properties after precipitation by ethanole and lyophilization:

a) pH stability (FIG. 1)

The enzyme was incubated at 20° C. in buffer solutions at various pH values for 66 hours. The activity of all trials was determined with 1 % hemicellulose at pH 4.8 as follows: 1 ml of 1 % substrate solution in Na citrate buffer (pH 4.8), (xylan from oat spelts; Sigma X-0627) was incubated at 50° C. for 2 min, and after addition of 0.5 ml of enzyme solution, at 50° C. for a further 15 min. Subsequently 3 ml of dinitro salicylic acid reagent (as FPU assay of IUPAC) and 0.5 ml of 2.5 N NaOH was mixed in, and the mixture was heated in a boiling waterbath for 5 min. It was subsequently cooled quickly in a cold waterbath, and the extinction at 540 nm was measured with the blank (citrate buffer) as reference. The extinction of the enzyme (0.5 ml of enzyme + 1.0 ml of citrate buffer) and of the substrate solution (1 ml of 1% substrate solution in citrate buffer) must be subtracted from this value. The calibration plot is constructed using 1.0 ml of citrate buffer and 0.5 ml of standard solution (containing 0.5-1.5 mg of xylose/ml).

Figure 2:
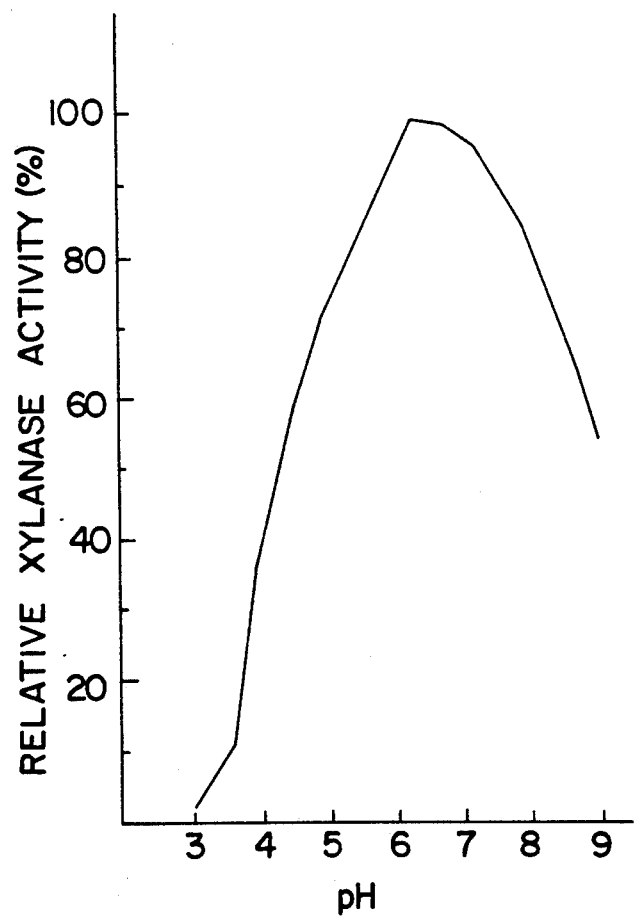

Calculation of the xylanase activity:

XU/ml = mg of reducing sugars (as xylose/test) × 0.888
97-100% of the original activity were obtained in a pH range of 5.0-7.0.

b) Optimal pH (FIG. 2)

Figure 3:
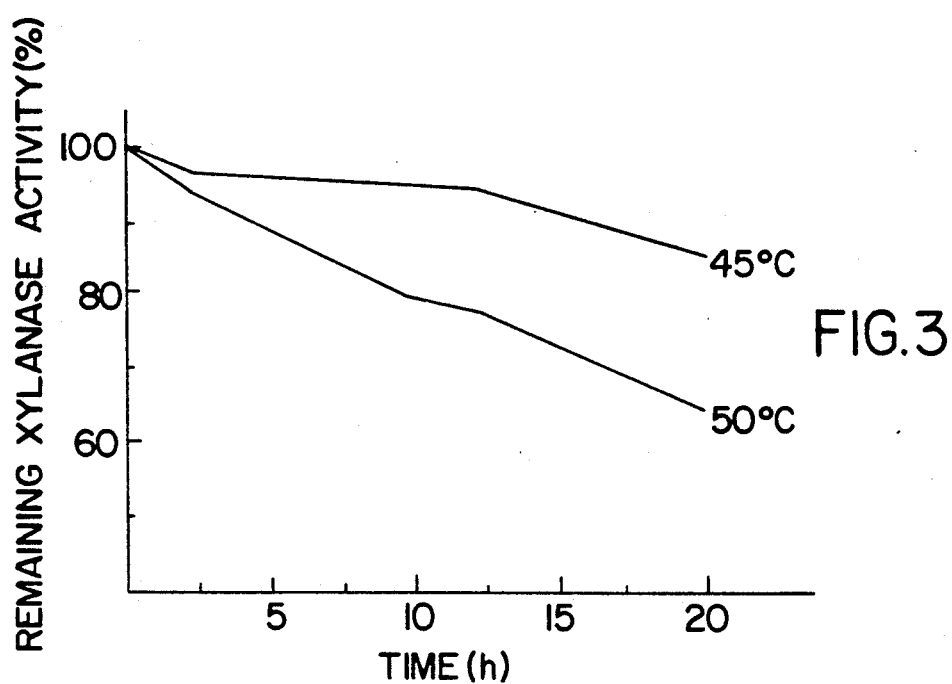

The enzyme activity was determined by incubation (50° C., 15 min) with 1% hemicellulose suspension in citrate buffer (pH 3.0-6.5), TrisHCl buffer (pH 7.0-9.0) and phosphate buffer (pH 6.5-8.0).
Optimal pH range: 6.0-7.5 c) Thermal stability (FIG. 3)

The enzyme solution was incubated in 0.05 molar citrate buffer (pH 4.8) at temperatures of 45°-60° C. for 0-72 hours. The activity of the enzyme was measured with 1% hemicellulose at 50° C.

Figure 4:
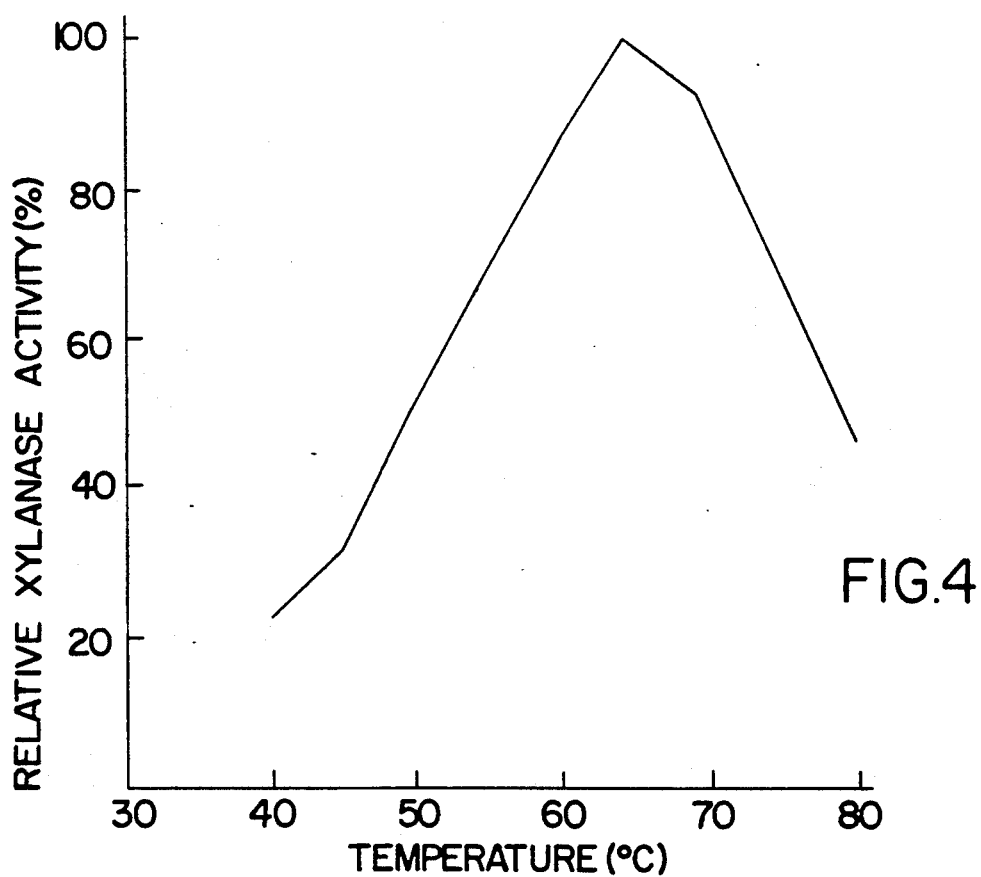

Measurement after 20 hours at a temperature of 45° C. showed 93%, and at a temperature of 50° C. showed 65%, of the original activity.

d) Optimal temperature (FIG. 4)

The enzyme activity was determined by incubation with a 1% hemicellulose suspension in 0.05 molar citrate buffer at pH 4.8 for 15 min.
Optimal temperature: 65° C.

e) Content of exo- and endocellulases and of β-glucosidase of an enzyme solution having an activity of 385 XU/ml:

i) exo- and endocellulases:
No cellulase activity was detected in the FPU assay of IUPAC. Furthermore, a dialysis tube (regenerated cellulose) was treated for 72 hours with the enzyme in an aqueous medium, and the medium was tested for the presence of glucose but no glucose was found. Cellulase-containing enzymes dissolve the dialysis tube within a few hours, by contrast. In addition, the nature of the reducing sugars liberated during a lengthy incubation of the enzyme on cellulose at a pH of 6.5 was determined.

The measurements were carried out in this case after 3, 7, 19 and 163 hours. It emerged from this that in all cases only xylose, xylobioses and xylotrioses but no glucose had been liberated. A replica technique was used to test for endocellulase activities with OBR - hydroxyethylcellulose-stained agar gel, no activity being found. The enzyme was shown by all the experiments and assays carried out to be completely free of cellulases.

The xylanase according to the invention showed no carboxymethylcellusase activity (endo-β-1,4-cellulase), at a determination limit of 0.1 unit/ml, and can therefore also be employed for the production of viscose.

ii) β-glucosidase:
0.6 ml of 0.05 molar sodium citrate buffer (pH 4.8) and 0.3 ml of enzyme solution were preincubated at 50° C. for 2 min. Subsequently 0.3 ml of p-nitrophenyl β-D-glucoside (4 mg/ml of sodium citrate buffer) was added, and the mixture was incubated at 50° C. for 10 min. The reaction was stopped by adding 2.4 ml of 1 molar $Na_2CO_3$ solution, and the extinction at 405 mm was measured with the blank as reference. The activity of β-glucosidase was calculated as follows:

$$IU/ml = \frac{E \times 12}{18.5 \times t}$$

$E$ ... extinction $t$ ... reaction time (minutes)

The xylanase according to the invention had a β-glucosidase activity of 0.2-0.9 IU/ml.

The content of β-glucosidase, which cleaves cellobiose into glucose, has no effect on the behavior of the xylanase according to the invention in the production of cellulose because the absence of exo- and endocellulases means that no cellulose breakdown products which could be attacked by β-glucosidase are formed.

f) In addition, the beta-xylosidase, arabinosidase, acetylesterase, acetylxylan esterase and mannanase activity was found to be ≦100 units/1 in each case.

g) The content of soluble protein in the enzyme was 800 mg/l, the molecular weight of the main protein was 24 to 25 kDa and the isoelectric point of the main protein was 4.1.

h) The purified enzyme was hydrolyzed enzymatically to 11 peptides 4 peptides with 8, 16, 5 and 12 amino acids respectively were sequenced. It emerged from this that the investigated xylanase was blocked at the N terminus, and thus it was not possible to start sequencing from the N-terminal end, whereas xylanase isolated from Humicola lanuginosa (=Thermomyces lanuginosus) according to Anand et al., Arch. Biochem. Biophys 276, 546-553 (1990) contained arginine as N-terminal amino acid.

The xylanase prepared according to the invention is used for the enzymatic treatment of xylan- and lignocellulose-containing vegetable raw materials and fibers composed of such raw materials and can, for example, advantageously be employed for bleaching, for deinking, for refining cellulose in the production of viscose or for another pretreatment such as, for example, removal of xylan before digestion.

By xylan- and lignocellulose-containing vegetable raw materials are meat raw materials from deciduous and coniferous trees, annual plants, for example flax, straw, bagasse, kenaf, reeds, elephant grass etc., but also fibers from vegetable raw materials such as bleached, semibleached or unbleached pulp or waste paper.

It is not necessary for the xylanase prepared according to the invention to be purified for use, it suffices to remove the solid nutrient medium. After removal of the solid nutrient material, the fermentation broth can be employed as such directly for the treatment of fibers composed of vegetable raw materials.

When employed in the cellulose industry, it is possible to treat unbleached as well as semibleached as well as bleached pulp with the xylanase prepared according to the invention. The treatment of the pulp results in hemicellulose-lignin linkages being broken. Less bleach is thus used in the subsequent bleaching process. On treatment of semibleached pulp, the xylan remaining after the preliminary bleaching is broken down, which results in cleaner and paler pulps. The effect of the enzyme treatment is determined by means of the kappa number (K) which indicates the content of oxidizable substances, that is to say lignin, for example. A higher alpha-cellulose content is reached in the bleached pulp owing to the xylanase treatment.

EXAMPLE 1

300 ml of medium consisting of 9 g of ground and dried corn cobs, 3.3 g of meat peptone, 0.6 g (NH$_4$)$_2$SO$_4$, 0.45 g urea, 0.09 g MgSO$_4$·7H$_2$O, 0.09 g CaCl$_2$·2H$_2$O, 4.5 g KH$_2$PO$_4$, 0.3 ml Tween 80, 0.3 ml S$_1$ (1.6 g/l MnSO$_4$·H$_2$O; 3.45 g/l ZnSO$_4$·7H$_2$O; 2.0 g/l CaCl$_2$·6H$_2$O) and 0.3 ml S$_2$ (5 g/l FeSO$_4$·7H$_2$O) were adjusted to a pH of 6 and autoclaved in a shaking flask at 128° C. for 60 min. *Thermomyces lanuginosus* DSM 5826 preculture was inoculated into this medium and cultivated at 50° C. while shaking (140 rpm) for 4.5 days.

After 4.5 days, the mixture was filtered, and the activity of xylanase (XU/ml), β-glucosidase (IU/ml), carboxymethylcellulase (CMC-ase/ml) and exo glucanase (FPU/ml) was determined.

| | |
|---|---|
| XU/ml | 389.7 |
| after storing 3 days at 4° C. | 395.0 |
| IU/ml | 0.29 |
| FPU/ml | not detectable |
| CMC-ase/ml | not detectable |

EXAMPLE 2

Corn cobs were
a) shredded (size of the pieces of corn cob above 10 mm)
b) coarsely ground (size of the pieces of corn cob between 3 and 10 mm)
c) finely ground (size of the pieces of corn cob below 3 mm)

In each case 1000 ml of a medium consisting of 28,6g of yeast extract, 4.23 g of (NH$_4$)$_2$SO$_4$, 10 g of KH$_2$PO$_4$, 0.3 g of FeSO$_4$·7H$_2$O, 0.3 g of MgSO$_4$·7H$_2$O and 0.3 g of CaCl$_2$·2H$_2$O and 25 g of a) shredded, b) coarsely ground and c) finely ground, dried corn cobs were prepared, adjusted to a pH of 6.5 and autoclaved in a shaking flask at 121° C. for 25 minutes. *Thermomyces lanuginosus* DSM 5826 preculture was inoculated into these media and cultivated at 50° C. with shaking. After 5 days, filtration was carried out, and the xylanase activity (XU/ml) in the various media was determined:

| Corn cobs | XU/ml | after storing 1 day at 4° C. XU/ml |
|---|---|---|
| Shredded | 764 | 881 |
| Coarsely ground | 1601 | 1526 |
| Finely ground | 388 | 423 |

EXAMPLE 3

The following xylanase activities were determined in the medium described in Example 2 and in the manner described there, but using other C sources:

| C source | Xylanase activity (XU/ml) |
|---|---|
| Corn cobs (50% finely ground, 50% coarsely ground) | 477 |
| Wheat straw | 232 |
| Wheat bran | 186 |
| Barley spelts | 61 |
| *Ulva rifide* (alga) | 28 |
| Alfalfa meal | 20 |
| Red clover/grass meal | 14 |
| Beech bark, ground | 8 |
| Soluble starch | 4 |
| Soya bean oil | 4 |

EXAMPLE 4

*Thermomyces lanuginosus* DSM 5826 was cultivated as in Example 1, employing 9 g of ground wheat straw in place of ground corn cobs.

| | |
|---|---|
| XU/ml | 104.3 |
| after storing 3 days at 4° C. | 123.9 |
| IU/ml | 0.51 |
| FPU/ml | Not detectable |
| CMC-ase/ml | Not detectable |

EXAMPLE 5

*Thermomyces lanuginosus* DSM 5826 was cultivated as in Example 1, employing barley spelts in place of ground corn cobs.

| | |
|---|---|
| XU/ml | 222.9 |
| after storing 3 days at 4° C. | 196.2 |
| IU/ml | 0.60 |
| FPU/ml | Not detectable |
| CMC-ase/ml | Not detectable |

EXAMPLE 6

*Thermomyces lanuginosus* DSM 5826 was cultivated as in Example 1, employing 9 g hemicellulose (xylan) in place of ground corn cobs.

| | |
|---|---|
| XU/ml | 151.55 |
| IU/ml | not detectable |
| FPU/ml | not detectable |
| CMC-ase/ml | not detectable |

EXAMPLE 7

TREATMENT OF SULFATE PULP

Dried sulfate pulp from ruzomberok (hardwood) was heated and shaken with water at 45° C. for 1.5 hours. Subsequently xylanase, prepared in analogy to Example 1, was added and shaken at 230 rpm.

| a) 30 g of fermentation broth | b) 90 g of fermentation broth |
|---|---|
| 220 g of pulp (K = 19.97) | 220 g of pulp (K = 19.97) |
| 350 g of water | 290 g of water |
| 100 XU enzyme were added per gram of fibers | 300 XU enzyme were added per gram of fibers |

After removal of the pulp by filtration, the kappa number was determined.

|  | a) | b) |
|---|---|---|
| Kappa number | 17.45 | 13.39 |

What we claim is:

1. A process for the preparation of xylanase, comprising cultivating *Thermomyces lanuginosus* which contains corn cobs.

2. The process of claim 1, wherein the *Thermomyces lanuginosus* is DSM 5826.

3. The process of claim 1, comprising cultivating at a temperature of 30°–70° C. and at a pH of 5.0 to 8.0.

4. The process of claim 1, comprising cultivating at a temperature of 45° to 55° C. and at a pH of 5.0 to 8.0.

5. The process of claim 1, comprising cultivating *Thermomyces lanuginosus* is DSM 5826 at a temperature of 45° to 55° C. and at a pH of 6.0 to 7.0.

* * * * *

UNITED STATES PATENT AND TRADEMARK OFFICE
CERTIFICATE OF CORRECTION

PATENT NO. : 5,183,753

DATED : February 2, 1993

INVENTOR(S) : Wolfgang WIZANI et al.

It is certified that error appears in the above-identified patent and that said Letters Patent is hereby corrected as shown below:

Claim 1, Column 8, line 8, after "lanuginosus" insert --in a nutrient medium--.

Signed and Sealed this

Eighteenth Day of January, 1994

BRUCE LEHMAN

*Attesting Officer*  *Commissioner of Patents and Trademarks*